DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED APRIL 3, 1973

909 O.G. 8

T909,012

NOVEL 2,2 - DISUBSTITUTED-4-(1,1-DIALKYL-2-ETHANOL)-1,3-DIOXOLANES AND PROCESS FOR THEIR PRODUCTION

Anthony W. McCollum, 404 Hillmont, Longview, Tex. 75601

Filed July 28, 1972, Ser. No. 275,998
Int. Cl. C07d *13/04*
U.S. Cl. 260—340.9
No Drawing. 12 Pages Specification

Water - insoluble 2,2-disubstituted-4-(1,1-dialkyl-2-ethanol)-1,3-dioxolane compounds having the formula

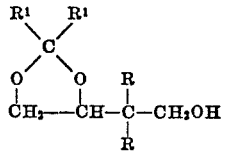

wherein each R is selected from the group consisting of hydrogen or a lower straight or branched chain alkyl of 1 to 4 carbons, and each $R^1$ is selected from the group consisting of straight or branched chain alkyl of 1 to 10 carbon atoms, substituted or unsubstituted phenyl, or $—CH=CH_2$;

are prepared by the process which comprises reacting a triol compound having the formula

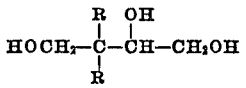

wherein each R is as defined hereinabove, at a temperature of between about 40° C. and about 150° C. in the presence of an acid catalyst such as p-toluenesulfonic acid with at least an equal molar amount of a carbonyl compound having the formula

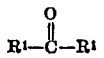

wherein each $R^1$ is as defined hereinabove.